United States Patent
DeLucia et al.

(10) Patent No.: US 6,869,670 B2
(45) Date of Patent: Mar. 22, 2005

(54) COMPOSITES MATERIAL WITH IMPROVED HIGH VISCOSITY FLUID INTAKE

(75) Inventors: Mary Lucille DeLucia, Roswell, GA (US); Sandy Chi-Ching Tan, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 27 days.

(21) Appl. No.: 09/871,031

(22) Filed: May 31, 2001

(65) Prior Publication Data

US 2002/0182396 A1 Dec. 5, 2002

(51) Int. Cl.$^7$ ............................................. B32B 27/04
(52) U.S. Cl. ................... 428/297.4; 428/198; 428/367; 428/373; 428/397; 604/358; 604/367
(58) Field of Search ................... 428/297.4, 411.1, 428/373, 198, 397; 604/358, 367, 389; 264/45.1

(56) References Cited

U.S. PATENT DOCUMENTS

| | | | |
|---|---|---|---|
| 3,338,992 A | 8/1967 | Kinney | 264/64 |
| 3,341,394 A | 9/1967 | Kinney | 161/72 |
| 3,502,763 A | 3/1970 | Hartmann | 264/210 |
| 3,542,615 A | 11/1970 | Dobo et al. | 156/181 |
| 3,692,618 A | 9/1972 | Dorschner et al. | 161/72 |
| 3,802,817 A | 4/1974 | Matsuki et al. | 161/169 |
| 3,849,241 A | 11/1974 | Butin et al. | 161/169 |
| 4,340,563 A | 7/1982 | Appel et al. | 264/518 |
| 4,600,620 A * | 7/1986 | Lloyd et al. | 428/195 |
| 4,605,402 A | 8/1986 | Iskra | 604/368 |
| 5,057,368 A | 10/1991 | Largman et al. | 428/397 |
| 5,069,970 A | 12/1991 | Largman et al. | 428/373 |
| 5,108,820 A | 4/1992 | Kaneko et al. | 428/198 |
| 5,108,827 A | 4/1992 | Gessner | 428/287 |
| 5,272,236 A | 12/1993 | Lai et al. | 526/348.5 |
| 5,277,976 A | 1/1994 | Hogle et al. | 428/397 |
| 5,294,482 A | 3/1994 | Gessner | 428/219 |
| 5,322,728 A | 6/1994 | Davey et al. | 428/296 |
| 5,336,552 A | 8/1994 | Strack et al. | 428/224 |
| 5,466,410 A | 11/1995 | Hills | 264/172.11 |
| 5,536,555 A | 7/1996 | Zelazoski et al. | 428/138 |
| 5,567,501 A | 10/1996 | Srinivasan et al. | 428/137 |
| 5,571,619 A | 11/1996 | McAlpin et al. | 428/364 |
| 5,643,240 A * | 7/1997 | Jackson et al. | 604/378 |
| 5,707,468 A | 1/1998 | Arnold et al. | 428/224 |
| 5,804,021 A | 9/1998 | Abuto et al. | 156/252 |
| 5,830,548 A * | 11/1998 | Andersen et al. | 428/36.4 |
| 5,853,403 A * | 12/1998 | Tanzer et al. | 604/385.1 |
| 5,868,724 A | 2/1999 | Dierckes, Jr. et al. | 604/368 |
| 5,873,868 A | 2/1999 | Nakahata | 604/383 |
| 5,883,028 A | 3/1999 | Morman et al. | 442/394 |
| 5,906,879 A * | 5/1999 | Huntoon et al. | 428/136 |
| 5,977,430 A * | 11/1999 | Roe et al. | 604/378 |
| 6,018,093 A | 1/2000 | Roe et al. | 604/367 |
| 6,267,975 B1 * | 7/2001 | Smith, III et al. | 424/401 |
| 6,420,625 B1 * | 7/2002 | Jones et al. | 604/367 |

FOREIGN PATENT DOCUMENTS

| | | | |
|---|---|---|---|
| EP | 0 441 064 A1 | 8/1991 | A61F/13/15 |
| EP | 0 586 924 | 10/1997 | |
| EP | 0 617 940 | 11/1999 | |
| GB | 2 284 786 | 6/1995 | A61F/13/15 |

* cited by examiner

*Primary Examiner*—Bruce H. Hess
*Assistant Examiner*—Camie S Thompson
(74) *Attorney, Agent, or Firm*—Pauley Petersen & Erickson

(57) ABSTRACT

A liner system suitable for use in personal care absorbent products having a composite material including a substructure applied to a first layer. The first layer and the substructure define a plurality of voids for accommodating passage of fluids through the composite material. In one embodiment, high viscosity fluids including the particles contained therein pass through a plurality of apertures in the first layer. The voids defined by the first layer and the substructure entrap the particles to accommodate passage of fluids through the composite material.

27 Claims, 3 Drawing Sheets

COMPOSITES MATERIAL WITH IMPROVED HIGH VISCOSITY FLUID INTAKE

BACKGROUND OF THE INVENTION

Conventional liners used in personal care absorbent articles do not provide for high viscosity fluids containing particles, for example menses or runny bowel movements. As a result, the conventional liners used in personal care absorbent articles leak and contribute to poor skin health. Many conventional liners absorb water from the high viscosity fluids. However, these conventional liners generally do not provide for particle intake. As a result, the particles contained within the high viscosity fluids separate during absorption of the water and tend to remain on the surface of the liner to produce undesired interactions with the wearer's skin.

SUMMARY OF THE INVENTION

In response to the discussed difficulties and problems encountered in the prior art, a composite material suitable for use as a liner system in personal care absorbent products for accommodating passage of fluids through the composite material has been discovered.

The composite material includes a first layer, suitably a film, a film and fiber combination, or a spunbond material having a basis weight of about 0.3 osy to about 2.5 osy, more particularly about 0.44 osy to about 1.0 osy.

In one embodiment of this invention, the first layer includes a plurality of slits or apertures which extend through it to permit the passage of fluids, for example high viscosity fluids including the particles contained therein, through the first layer. Desirably, the first layer forming the apertures has a z-direction orientation to direct fluid flow through the first layer and prevent rewet or fluid flow back through the first layer. The first layer may be made of a hydrophobic material to further direct fluid flow through the first layer and prevent the separation and collection of the fluid and the particles at a surface of the first layer which may contact the skin of the wearer.

The apertures may have a diameter of about 100 microns to about 10,000 microns and can be formed by several conventional methods, including, but not limited to, die cutting, pin embossing, and thermal embossing.

The composite material further includes a substructure applied to the first layer. For example, the substructure may be bonded to the first layer using thermal bonding, adhesive bonding, and/or other bonding techniques well known in the art. The substructure can be pleated, corrugated, thremoformed or embossed and has a high modulus and high resiliency to maintain its structure during packaging and use.

Desirably, the substructure is a three-dimensional nonwoven material or web. Meltblown and spunbond fibrous nonwoven webs work particularly well as materials from which to form the substructure. A particularly well-suited spunbond nonwoven web for the substructure is made from sheath/core or side-by-side polyethylene/polypropylene spunbond bicomponent fibers.

The first layer and the substructure define a plurality of voids for accommodating passage of fluids through the composite material. In one embodiment of this invention, the voids form a plurality of compartments desirably having a generally triangular cross section area to accommodate passage of fluids through the composite material. Desirably, the compartments have a maximum height of about 0.1 cm to about 2.0 cm and a maximum width of about 0.1 cm to about 2.0 cm.

The composite material may be generally applied to or entangled with an absorbent core. Further, the composite material may be bonded or laminated to the absorbent core. As the high viscosity fluid moves through the first layer into the substructure, the particles are separated from the fluid and are entrapped within the voids formed in the composite material. The fluid is absorbed through the substructure and into the absorbent core to prevent leakage and rewet. A liquid impermeable outer cover may be positioned on the other side of the absorbent core (opposite the liner) to prevent water absorption through the absorbent core and into the surrounding environment, for example, clothing or a bedding sheet.

With the foregoing in mind, it is a feature and advantage of the invention to provide a liner system for use in personal care absorbent products that accommodates fluid passage through the composite material, including masking high viscosity fluids containing particles.

It is also a feature and advantage of the invention to provide a liner system for use in personal care absorbent products wherein fluids are absorbed and separated from the particles contained therein as the fluids pass through the liner system.

It is also a feature and advantage of the invention to provide a liner system for use in personal care absorbent products having a plurality of voids for containing and managing high viscosity fluids containing particles.

DEFINITIONS

As used herein, the term "film" refers to a thermoplastic film made using a film extrusion and/or forming process, such as a cast film or blown film extrusion process. The term includes apertured films, slit films, and other porous films which constitute liquid transfer films, as well as films which do not transfer liquid. The term also includes film-like materials that exist as open-celled foams.

As used herein, the term "nonwoven fabric or web" means a web having a structure of individual fibers or threads which are interlaid, but not in an identifiable manner, as in a knitted fabric. Nonwoven fabrics or webs have been formed from many processes such as, for example, meltblowing processes, spunbonding processes, and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91).

As used herein, the term "spunbond fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, and U.S. Pat. No. 3,542,615 to Dobo et al. Spunbond fibers are generally not tacky when they are deposited onto a collecting surface. Spunbond fibers are generally continuous and have average diameters (from a sample of at least 10) larger than 7 microns, more particularly, between about 10 and 20 microns. The fibers may also have shapes such as those described in U.S. Pat. No. 5,277,976 to Hogle et al., U.S. Pat. No. 5,466,410 to Hills, and U.S. Pat. Nos. 5,069,970 and 5,057,368 to Largman et al., which describe hybrids with unconventional shapes.

As used herein, the term "meltblown fibers" means fibers formed by extruding a molten thermoplastic material through a plurality of fine, usually circular, die capillaries as molten threads or filaments into converging high velocity, usually hot, gas (for example, air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al. Meltblown fibers are microfibers which may be continuous or discontinuous, are generally smaller than 10 microns in average diameter, and are generally tacky when deposited onto a collecting surface.

As used herein, the term "polymer" generally includes, but is not limited to, homopolymers, copolymers, such as for example, block, graft, random and alternating copolymers, terpolymers, etc., and blends and modifications thereof. Furthermore, unless otherwise specifically limited, the term "polymer" shall include all possible geometric configurations of the molecule. These configurations include, but are not limited to, isotactic, syndiotactic and random symmetries.

"Bicomponent fibers" refers to fibers which have been formed from at least two polymers extruded from separate extruders but spun together to form one fiber. The polymers are arranged in substantially constantly positioned distinct zones across the cross-section of the bicomponent fibers and extend continuously along the length of the bicomponent fibers. The configuration of such a bicomponent fiber may be, for example, a sheath/core arrangement wherein one polymer is surrounded by another or may be a side-by-side arrangement or an "islands-in-the-sea" arrangement. Bicomponent fibers are taught in U.S. Pat. No. 5,108,820 to Kaneko et al., U.S. Pat. No. 5,336,552 to Strack et al., and European Patent 0586924. For two component fibers, the polymers may be present in ratios of 75/25, 50/50, 25/75 or any other desired ratios.

As used herein, the term "biconstituent fibers" refers to fibers which have been formed from at least two polymers extruded from the same extruder as a blend. Biconstituent fibers do not have the various polymer components arranged in relatively constantly positioned distinct zones across the cross-sectional area of the fiber and the various polymers are usually not continuous along the entire length of the fiber, but rather typically form fibrils or protofibrils which start and end at random. Biconstituent fibers are sometimes also referred to as multiconstituent fibers. Fibers of this general type are taught, for example, by U.S. Pat. Nos. 5,108,827 and 5,294,482 to Gessner.

As used herein, the term "bonded carded web" refers to webs made from staple fibers which are sent through a combing or carding unit, which breaks apart and aligns the staple fibers in the machine direction to form a generally machine direction-oriented fibrous nonwoven web. Such fibers are usually purchased in bales which are placed in a picker which separates the fibers prior to the carding unit. Once the web is formed, it is then bonded by one or more of several known bonding methods. One such bonding method is powder bonding, wherein a powdered adhesive is distributed through the web and then activated, usually by heating the web and adhesive with hot air. Another suitable bonding method is pattern bonding, wherein heated calender rolls or ultrasonic bonding equipment are used to bond the fibers together, usually in a localized bond pattern, though the web can be bonded across its entire surface, if so desired. Another suitable and well-known bonding method, particularly when using bicomponent staple fibers, is through-air bonding.

As used herein, the term "personal care product" or "personal care absorbent product" means feminine hygiene products, diapers, training pants, absorbent underpants, adult incontinence products, wipes, wound care products, including bandages, and the like.

As used herein, the term "thermoplastic" describes a material that softens when exposed to heat and which substantially returns to a nonsoftened condition when cooled to room temperature.

These terms may be defined with additional language in the remaining portions of the specification.

DETAILED DESCRIPTION

Figure 1:
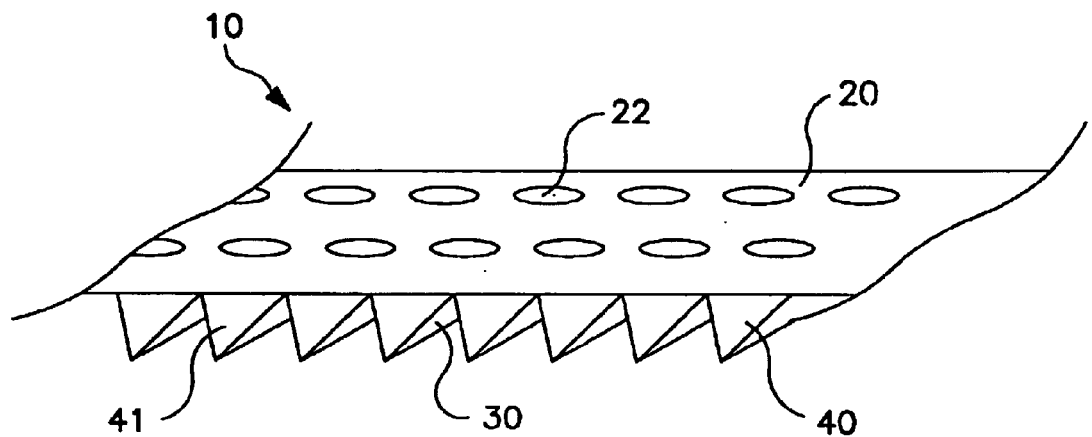
FIG. 1 is a perspective view of an exemplary composite material having a substructure applied to a first layer, in accordance with one embodiment of this invention.
Figure 2:
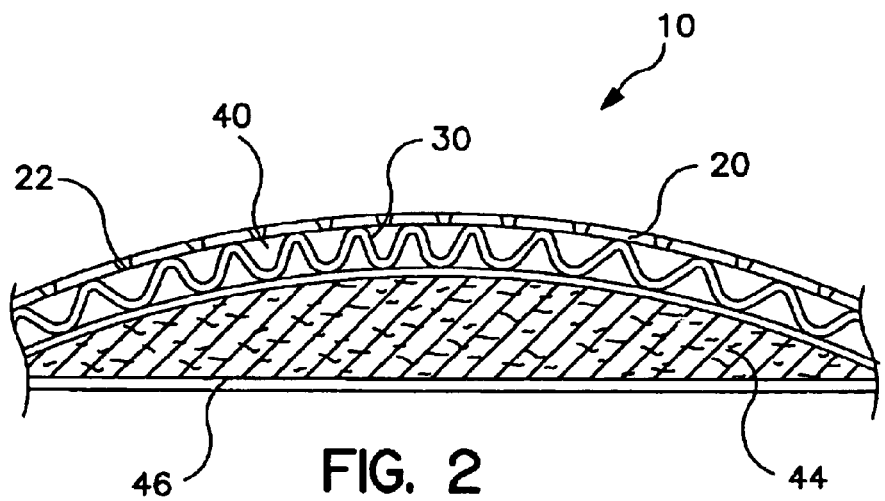
FIG. 2 is a sectional view of an exemplary personal care absorbent product having a composite material, in accordance with one embodiment of this invention.

According to this invention, a composite material 10 suitable for use as a liner system in personal care absorbent products for accommodating passage of fluids through the composite material 10 is shown in FIGS. 1 and 2. In one embodiment of this invention, the composite material 10 is particularly suitable for masking high viscosity fluids containing particles. Although references made herein are directed to personal care absorbent products, it is apparent to one having ordinary skill in the art that the composite material 10 in accordance with this invention may be used for articles or products other than personal care absorbent products. Such articles or products include, but are not limited to, fabrics for conveying fluids, spacer layers, fasteners, filter media for liquid and air filtration applications, facemasks, wipes and the like. For example, fabrics that deliver a cream or a soap, wipes impregnated with cleaning agents, cleaning products which scrub and convey material away from the surface being cleaned, and other products that rely on porosity and topography to function.

The composite material 10 of this invention includes a first layer 20, for example a thermoplastic liner. The first layer 20 is illustrated as overlying an outer cover 46 and an absorbent core 44 (FIG. 2), and may but need not have the same dimensions as the outer cover 46 or the absorbent core 44. The first layer 20 is desirably compliant, soft feeling, and non-irritating to the wearer's skin. Further, the first layer 20 can be less hydrophilic than the absorbent core 44, to present a relatively dry surface to the wearer and permit liquid to readily penetrate through its thickness. In one embodiment of this invention, the first layer 20 is a shrinkable first layer having a basis weight of about 0.3 osy to about 2.5 osy, more particularly about 0.44 osy to about 1.0 osy. The shrinkable first layer 20 may be heated to produce the composite material 10 as described below.

In one embodiment of this invention, suitable for runny bowel movement separation and containment, and menses management and containment, the first layer 20 includes a plurality of slits or apertures 22. As shown in FIGS. 1 and 2, at least a portion of the first layer 20 includes the apertures 22 which extend through the first layer 20 to permit the passage of the high viscosity fluids including the particles which may be contained therein through the first layer 20. Desirably, the first layer 20 forming the apertures 22 has a z-direction orientation to direct fluid flow through the first layer 20 and prevent rewet or fluid flow back through the first layer 20. In one embodiment of this invention, the first layer 20 is hydrophobic to further direct fluid flow through the first layer 20 and prevent the separation and collection of the fluid and/or the particles at a surface of the first layer 20 contacting the skin of the wearer.

The apertures 22 may have a diameter of about 100 microns to about 10,000 microns and can be formed by several conventional methods, including, but not limited to, die cutting, pin embossing, and thermal embossing.

The apertured first layer 20 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, plastic films, or the like. Various woven and non-woven fabrics can be used for the apertured first layer 20. For example, the apertured first layer 20 can be composed of a meltblown or spunbonded web of polyolefin fibers. The apertured first layer 20 can also be a bonded carded web composed of natural and/or synthetic fibers. The first layer 20 can be composed of a substantially hydrophobic material, and the hydrophobic material can, optionally, be treated with a surfactant or otherwise processed to impart a desired level of wettability and hydrophilicity. For example, the material can be surface treated with about 0.10 weight percent to about 0.50 weight percent, more desirably about 0.20 weight percent to about 0.40 weight percent of a surfactant commercially available from the Cognis Corp. of Ambler, Pa. and produced in Cincinnati, Ohio under the trade designation GLUCOPON. Other suitable surfactants can also be used. The surfactant can be applied by any conventional means, such as spraying, printing, brush coating or the like. The surfactant can be applied to the entire first layer 20 or can be selectively applied to particular sections of the first layer 20, such as the medial section along the longitudinal centerline.

A suitable liquid permeable apertured first layer 20 is a nonwoven bicomponent web having a basis weight of about 1 to about 100 grams per square meter (gsm), suitably about 20 to about 40 gsm, more suitably about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Desirably, the bicomponent fiber has a percentage of polymer components in the range of about 10–90% polyethylene/90–10% polypropylene, more desirably about 25–75% polyethylene/75–25% polypropylene, most desirably about 40–60% polyethylene/60–40% polypropylene. Other fiber orientations are possible, such as multi-lobe, side-by-side, end-to-end, or the like. While the outer cover 46 and the first layer 20 can include elastomeric materials, it can be desirable in some embodiments for the composite structure to be generally inelastic, where the outer cover 46, the first layer 20 and the absorbent core 44 include materials that are generally not elastomeric.

The first layer 20 can be formed from any suitable film-forming thermoplastic polymer. Examples of suitable polymers include without limitation polyethylene, polypropylene, copolymers of mainly ethylene and $C_3$–$C_{12}$ alpha-olefins (commonly known as linear low density polyethylene), copolymers of mainly propylene with ethylene and/or $C_4$–$C_{12}$ alpha-olefins, and flexible polyolefins including propylene-based polymers having both atactic and isotactic propylene groups in the main polypropylene chain. Other suitable polymers include without limitation elastomers, for example polyurethanes, copolyether esters, polyamide polyether block copolymers, ethylene vinyl acetate copolymers, block copolymers having the general formula A-B-A' or A-B such as copoly (styrene/ethylene-butylene), styrene-poly (ethylene-propylene)-styrene, styrene-poly (ethylene-butylene)-styrene, polystyrene/poly (ethylene-butylene)/polystyrene, poly (styrene/ethylene-butylene/styrene), and the like. Metallocene-catalyzed polyolefins are also useful, including those described in U.S. Pat. Nos. 5,571,619; 5,322,728; and 5,272,236, the disclosures of which are incorporated herein by reference.

The composite material 10 further includes a substructure 30 applied to the first layer 20. The substructure 30 may be pleated, corrugated, thermoformed or embossed and has a high modulus and high resiliency to maintain its structure during packaging and use. The substructure 30 may be laminated or bonded to the first layer 20 by using thermal bonding, adhesive bonding, and/or other bonding techniques well known in the art. Thermal point bonding or adhesive spiral bonding are desired because these bonding methods do not damage the substructure 30. The substructure 30 desirably has a basis weight of about 0.2 osy to about 2.0 osy, more desirably about 0.3 osy to about 1.5 osy.

Desirably, the substructure 30 is a three-dimensional nonwoven material or web. Meltblown and spunbond fibrous nonwoven webs work particularly well as materials from which to form the substructure 30. As discussed above, meltblown webs are made from fibers formed by extruding a molten thermoplastic material through a plurality of fine, usually circular dye capillaries as molten threads or filaments into a high-velocity heated air stream which attenuates the filaments of molten thermoplastic material to reduce their diameters. Thereafter, the meltblown fibers are carried by the high-velocity gas stream and are deposited on a collecting surface to form a web of randomly dispersed meltblown fibers.

As discussed above, spunbond nonwoven webs are made from fibers which are formed by extruding a molten thermoplastic material as filaments from a plurality of fine, usually circular, capillaries in a spinneret with the diameter of the extruded filaments then being rapidly reduced, for example, by non-eductive or eductive fluid-drawing or other well known spunbonding mechanisms. A well-suited spunbond nonwoven web for the substructure 30 is made from sheath/core or side-by-side polyethylene/polypropylene spunbond bicomponent fibers.

The first layer 20 and the substructure 30 define a plurality of voids for accommodating passage of fluids through the composite material 10. In embodiment of this invention, the plurality of voids 40 form a plurality of compartments 41 suitable for entrapping particles contained within high viscosity fluids which pass through the apertures 22 in the first layer 20. Desirably, the compartments 41 have a generally triangular cross section area and desirably provide enough void volume to accommodate the particles contained within the high viscosity fluids. Desirably, the compartments 41 have a maximum height of about 0.1 cm to about 2.0 cm. "Maximum height" refers to the distance measured from the apex to the base of the compartment 41, wherein the base of the compartment 41 is defined as the distance from one bonding point or bonding line of the substructure 30 with the first layer 20 to an adjacent bonding point or bonding line. The compartment 41 desirably has a maximum width of about 0.1 cm to about 2.0 cm. "Maximum width" refers to the distance measured from one bonding point or bonding line of the substructure 30 with the first layer 20 to an adjacent bonding point or bonding line, i.e. the length of the base.

Figure 3:
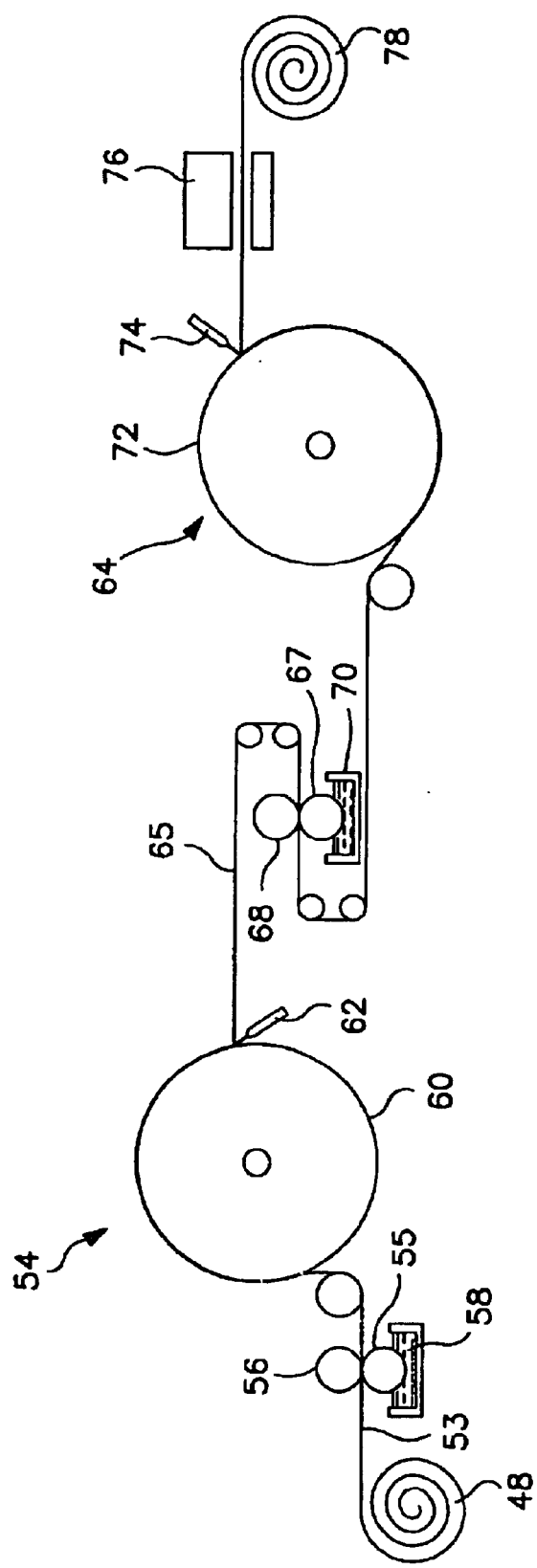
FIG. 3 is a schematic side view of one type of an apparatus for producing a substructure which, when applied to a first layer, defines a plurality of voids for accommodating passage of fluids through the composite material, in accordance with one embodiment of this invention.

The substructure 30 having structure and the plurality of voids 40 defined by the substructure 30 and the first layer 20 can be created by several different methods. For example, a first method of creating the substructure 30 involves creping a nonwoven web, as shown in FIG. 3. The nonwoven web may be any type of thermoplastic nonwoven web. For instance, the nonwoven web may be a spunbond web, a meltblown web, a bonded carded web, or a combination including any of the above. Desirably, the web is a spunbond web. A wide variety of thermoplastic polymer materials can be used to make the nonwoven web. Exemplary polymer materials include without limitation, polypropylene, polyethylene (high and low density), ethylene copolymers with $C_3$–$C_{20}$ α-olefins, propylene copolymers with ethylene or $C_4$–$C_{20}$ α-olefins, butene copolymers with ethylene, propylene, or $C_5$–$C_{20}$ α-olefins, polyvinyl chloride, polyesters, polyamides, polyfluorocarbons, polyurethane, polystyrene, polyvinyl alcohol, caprolactams, and cellulosic and acrylic resins. Bicomponent and biconstituent thermoplastic webs may also be utilized, as well as webs containing blends of one or more of the above-listed thermoplastic polymers. The web may have a basis weight of about 0.2–2.0 ounces per square yard (osy) before creping, desirably about 0.3–1.5 osy.

To begin the creping process, a nonwoven web 52 is unwound from a supply roll 48. The nonwoven web 52 is passed through a first creping station 54, a second creping station 64 or both.

As shown in FIG. 3, a first side 53 of the web 52 may be creped using the first creping station 54. The first creping station 54 includes a first printing station including a lower patterned or smooth printing roller 55, an upper smooth anvil roller 56, and a printing bath 58, and also includes a dryer drum 60 and associated creping or doctor blade 62.

The rollers 55 and 56 nip the web 52 and guide it forward. As the rollers 55 and 56 turn, the patterned or smooth printing roller 55 dips into the bath 58 containing an adhesive material, and applies the adhesive material to the first side 53 of the web 52 in a partial coverage at a plurality of spaced apart locations, or in a total coverage. The adhesive-coated web 52 is then passed around the drying drum 60 whereupon the adhesive-coated surface 53 becomes adhered to the drying drum 60. The first side 53 of the web 52 is then creped (i.e. lifted off the drum and bent) using the doctor blade 62.

A second side 65 of the web 52 may be creped using a second creping station 64, the same or similar to the first creping station 54, regardless of whether the first creping station 54 has been bypassed. The second creping station 64 includes a second printing station including a lower patterned or smooth printing roller 67, an upper smooth anvil roller 68, and a printing bath 70, and also includes a dryer drum 72 and associated creping or doctor blade 74.

The rollers 67 and 68 nip the web 52 and guide it forward. As the rollers 67 and 68 turn, the patterned or smooth printing roller 67 dips into the bath 70 containing an adhesive material, and applies the adhesive material to the second side 65 of the web 52 in a partial coverage at a plurality of spaced apart locations, or in a total coverage. The adhesive-coated web 52 is then passed around the drying drum 72 whereupon the adhesive-coated surface 65 becomes adhered to the drying drum 72. The second side 65 of the web 52 is then creped (i.e. lifted off the drum and bent) using the doctor blade 74.

After creping, the nonwoven web 52 may be passed through a chilling station 76 and wound onto a storage roll 78. The level of creping is affected by the surface speed of the storage roll 78 relative to the surface speed of the creping drum 72. The surface speed of the storage roll 78 is slower than the surface speed of the creping drum 72, and the difference between the two speeds affects the level of creping. The level of creping is a measurement of creping and is calculated according to the following equation:

$$\text{Crepe level (\%)} = \frac{S_d - S_s}{S_d} \times 100; \quad \text{Eq. (1)}$$

wherein $S_d$ is the surface speed of the creping drum and $S_s$ is the surface speed of the storage roll. The level of creping should generally be about 5–75%, preferably about 15–60%, most preferably about 25–50%.

A wide variety of adhesive bonding materials may be utilized to reinforce the fibers of the web 52 at the locations of adhesive application, and to temporarily adhere the web 52 to the surface of the dryer drum 60 and/or 72. Elastomeric adhesives (i.e. materials capable of at least 75% elongation without rupture) are especially suitable. Suitable materials include without limitation aqueous-based styrene butadiene adhesives, neoprene, polyvinyl chloride, vinyl copolymers, polyamides, and ethylene vinyl terpolymers. The presently desired adhesive material is an acrylic polymer emulsion sold by the B. F. Goodrich Company under the trade name HYCAR®. The adhesive may be applied using the printing technique described above, or may, alternatively, be applied by meltblowing, melt spraying, dripping, splattering, or any other technique capable of forming a partial or total adhesive coverage on the thermoplastic nonwoven web 52.

The creping of the nonwoven web 52 is primarily manifested in the bonded areas of the base ("raw") nonwoven web 52, corresponding to the nonwoven web bond pattern. As a result of the creping, the bonded regions are bent out of plane so as to cause permanent creping of the web 52, and the formation of filament looped regions in the unbonded regions alternating with (in between) the creped bonded regions.

The resulting creped nonwoven web 52 has low density, high permeability, excellent surface and bulk softness, recoverable stretch properties, surface topology, and permanent out-of-plane fiber orientation. The substructure 30 produced by the creping of the nonwoven web 52 is laminated to the first layer 20 to produce a plurality of voids 40.

Figure 4:
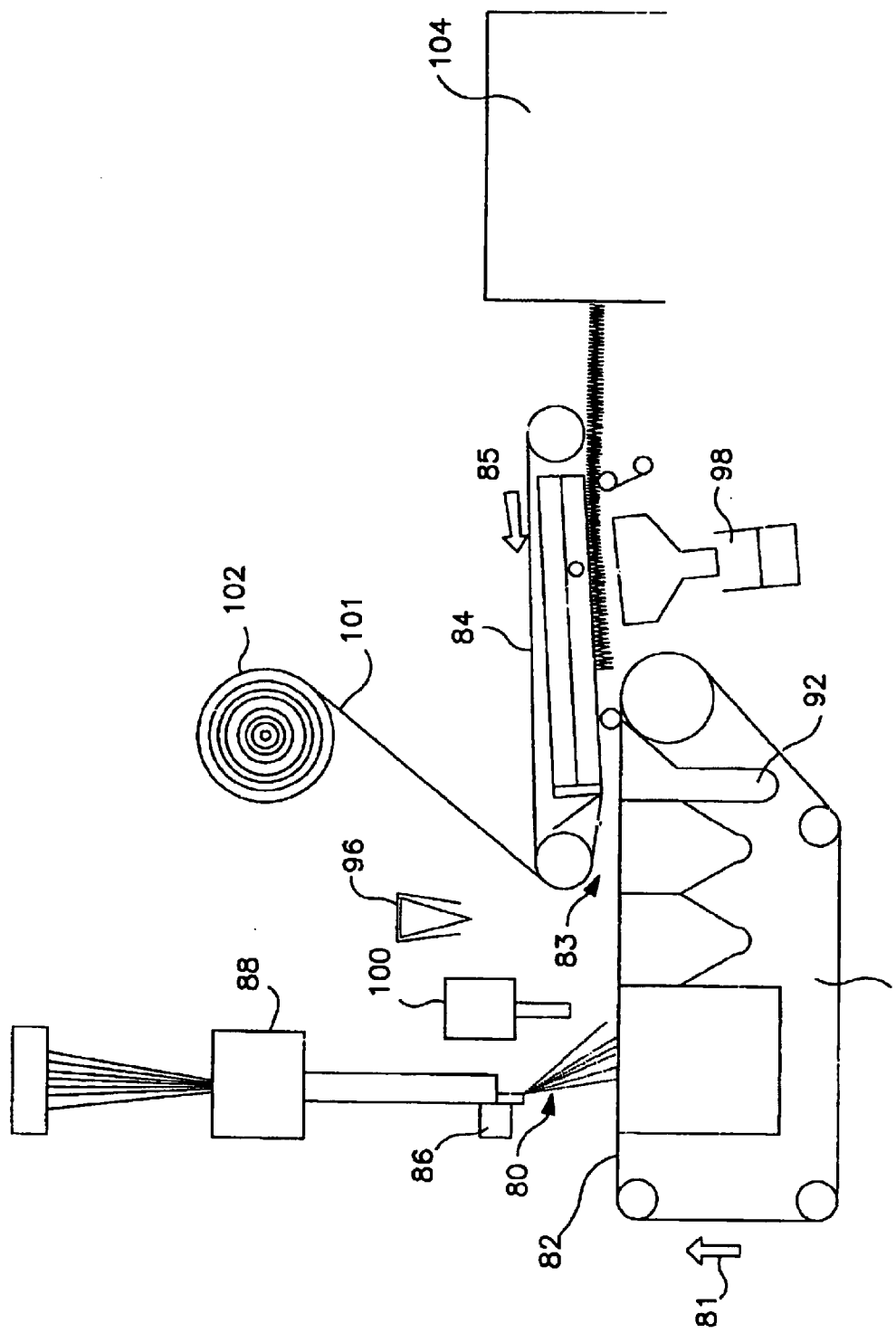
FIG. 4 is a schematic side view of one type of an apparatus for producing a substructure, which when applied to a first layer, defines a plurality of voids for accommodating passage of fluids through the composite material, in accordance with one embodiment of this invention.

As shown in FIG. 4, a second method for producing the voids 40 begins with transporting or conveying a base material 80 on a first moving surface 82 into a confined space defined by a nip 83 formed between the first moving surface 82 and a second moving surface 84. A coform unit 86 for adding additional material to the base material 80 is attached near an outlet of a fiber distribution unit 88.

The first moving surface 82 is moving in the direction of arrow 81 at a given speed. The base material 80 is held down on the first moving surface 82 by a hold down vacuum 90. As the base material 80 passes through the nip 83, the base material 80 is transferred to the second moving surface 84 moving in a direction indicated by arrow 85 via positive air pressure from a blow up box 92 positioned underneath the first moving surface 82 and a transfer vacuum 94 positioned beneath the second moving surface 84. The second moving surface 84 is moving at a speed slower than the speed of the first moving surface 82. In accordance with one embodiment of this invention, the speed of the first moving surface 82 is in the range of about 1.25 to about 7 times faster than the speed of the second moving surface 84.

The confining nature of the nip 83 is such that, as the base material 80 enters the nip 83 and is taken away at a slower speed by the second moving surface 84, the base material 80 accumulates in the nip 83, causing the fibers to bunch up and translate into a z-direction displacement until the volume of nip 83 is filled. More specifically, the base material 80 encounters a slowdown at the nip 83 as a result of which the base material 80 moves in the z-direction until it hits the second moving surface 84 and is removed thereby. As a result, the substructure 30 exiting from the nip 83 comprises at least one surface, and normally both surfaces, having ridges or peaks, as shown in FIG. 4.

Although suitable for producing ridged films and pleated wovens, this method is particularly suitable for producing preponderantly open, or low density, nonwoven webs of continuous fibers having z-direction components. Specifically, the substructure 30 produced in accordance with this method is a nonwoven web comprising a plurality of substantially continuous fibers having a z-direction orientation and forming the voids 40.

The substantially continuous fibers are preferably selected from the group consisting of homofilament fibers, bicomponent fibers, biconstituent fibers and combinations thereof. The substantially continuous fibers are preferably formed with polymers selected from the group consisting of polyolefins, polyamides, polyesters, polycarbonates, polystyrenes, thermoplastic elastomers, fluoropolymers, vinyl polymers, and blends and copolymers thereof.

Suitable polyolefins include, but are not limited to, polyethylene, polypropylene, polybutylene, and the like; suitable polyamides include, but are not limited to, nylon 6, nylon 6/6, nylon 10, nylon 12 and the like; and suitable polyesters include, but are not limited to, polyethylene terephthalate, polybutylene terephthalate and the like. Particularly suitable polymers for use in the present invention are polyolefins including polyethylene, for example, linear low density polyethylene, low density polyethylene, medium density polyethylene, high density polyethylene and blends thereof; polypropylene; polybutylene and copolymers as well as blends thereof. Additionally, the suitable fiber forming polymers may have thermoplastic elastomers blended therein. In addition, staple fibers may be employed in the nonwoven web as a binder. In one embodiment of this invention, bicomponent side-by-side polyethylene/polypropylene polymers are used.

In order to provide stability to the product material, the nonwoven web is bonded, either by application of an adhesive from adhesive system 96 or by thermal bonding such as by through-air bonding, a calender, or the like, or by means of a hot air knife 98. A hot air knife 100 is used to bond the individual polymer fibers together at various locations so that the web has increased strength and structural integrity for subsequent treatments such as passage through a through-air bonding (TAB) unit 104. A conventional hot air knife includes a mandrel with a slot that blows a jet of hot air onto the nonwoven web surface. Such hot air knives are taught, for example, by U.S. Pat. No. 5,707,468 to Arnold et al.

As shown in FIG. 4, the base material 80 of substantially continuous fibers is fed onto the first moving surface 82 from a fiber distribution unit 88. However, it will be apparent to those skilled in the art that certain base material fibers may be formed directly on the first moving surface 82 or unwound from prewound spools or the like.

Suitable base materials may be selected from the group consisting of spunbond, meltblown, spunbond-meltblown-spunbond laminates, coform, spunbond-film-spunbond laminates, bicomponent spunbond, bicomponent meltblown, biconstituent spunbond, biconstituent meltblown, pulp, superabsorbent, and combinations thereof.

The characteristics of the material produced in accordance with this method may be varied by varying such method elements as nip geometry, including the vertical distance between the first moving surface 82 and the second moving surface 84 as well as the extent of overlap between the first moving surface 82 and the second moving surface 84, vacuum strength and location, bonding mechanism, and speeds of the material entering and leaving the nip 83. The type of fiber will of course have an affect on the morphology of the web made. A second material 101 may be introduced into the nip 83 from the unwind designated by reference numeral 102.

A third method for producing the voids 40 involves the latent retraction of the first layer 20 after lamination of the substructure 30 to the first layer 20. The composite material 10 is formed by bonding the substructure 30 to the shrinkable first layer 20, for example a liner, which is made of a polymer or polymer blend having a shrinking point lower than the shrinking point of the polymer or polymer blend of the substructure 30. The composite material 10 is then heated to a temperature corresponding to the shrinking point of the first layer 20, causing the first layer 20 to shrink. This shrinkage results in bunching of the substructure 30, thus creating the voids 40 defined by the substructure 30 and the first layer 20.

A fourth method for producing the voids 40 involves the differential shrinkage of a melt spun material having fibers composed of one polymer with different characteristics or two different polymers, one having a lower shrinking point than the other polymer. Alternating rows of polymer pools are used to produce a melt spun web containing fibers of distinct polymer composition. The polymers can be chosen to exploit the differential shrinkage anticipated by the polymer properties. For example, a polyethylene copolymer and a polypropylene are melt spun to form a web. The web is subsequently shrunk by introducing heat to the web. Conventional means for introducing heat can be used, including but not limited to a hot air gun, a convection oven, or a through-air bonder. The polyethylene copolymer, which typically gives a softer fabric than the polypropylene, shrinks at a lower shrinking temperature than the polypropylene. As a result of applying heat to the substructure 30, the polypropylene puckers as the copolymer shrinks, to produce the voids 40.

A fifth method for producing the voids 40 involves the thermal pleating of a nonwoven web, desirably a spunbond nonwoven web, through a grooved roll. A thermoplastic nonwoven web is passed through a pressure nip. In one embodiment of this invention, the thermoplastic nonwoven web may be preheated. An embossing roll contacts a lower surface of the web and heats it to a temperature greater than the melting point of the thermoplastic fibers. A second roll contacts an upper surface of the web. As the web moves through the pressure nip, the web is pattern embossed to form autogenous thermal bonds which extend through the web. The autogenous bonded web is then creped by pressing the bonded web against a driven, grooved roll which feeds the web against a retarding member. The resulting structured or three-dimensional web forms the substructure 30 which is bonded to the first layer 20, thereby defining the voids 40 of the composite material 10.

As shown in FIG. 2, in one embodiment of this invention, the composite material 10 is bonded or laminated to the absorbent core 44, which is located between the composite material 10 and the outer cover 46. In one embodiment of this invention, a high viscosity fluid moves through the first layer 20 into the substructure 30, wherein particles contained in the fluid are separated from the fluid and are entrapped within the voids 40 formed in the composite material 10. The fluid is absorbed through the substructure 30 and into the absorbent core 44 to reduce leakage and rewet.

In the embodiment of the present invention as shown in FIG. 2, the absorbent core 44 is positioned between the outer cover 46 and the first layer 20. The absorbent core 44 may be joined with at least one of the outer cover 40 and the first layer 20 by any suitable means, such as adhesives, as is well known in the art. The absorbent core 44 can be any suitable structure which is generally compressible, conformable, and capable of absorbing and retaining liquids and certain body wastes.

The absorbent core 44 can be manufactured in a wide variety of sizes and shapes, and from a wide variety of liquid absorbent materials commonly used in the art. For example, the absorbent core 44 can suitably include a matrix of hydrophilic fibers, such as a web of cellulosic fluff, mixed with particles of a high-absorbency material commonly known as superabsorbent material. In a particular embodiment, the absorbent core 44 includes a matrix of cellulosic fluff, such as wood pulp fluff, and superabsorbent hydrogel-forming particles. The wood pulp fluff can be exchanged with synthetic, polymeric, meltblown fibers or with a combination of meltblown fibers and natural fibers. The superabsorbent particles can be substantially homogeneously mixed with the hydrophilic fibers or can be non-uniformly mixed. The fluff and superabsorbent particles can also be selectively placed into desired zones of the absorbent core 44 to better contain and absorb body exudates. The concentration of the superabsorbent particles can also vary through the thickness of the absorbent core 44. Alternatively, the absorbent core 44 can include a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent core 44 is generally rectangular in shape, and includes a blend of wood pulp fluff and superabsorbent material. One preferred type of fluff is identified with the trade designation CR1654, available from Kimberly-Clark Corporation, Neenah, Wis., U.S.A., and is a bleached, highly absorbent sulfate wood pulp containing primarily soft wood fibers. As a general rule, the superabsorbent material is present in the absorbent core 44 in an amount of from about 5 to about 90 weight percent based on total weight of the absorbent core 44. The absorbent core 44 suitably has a density within the range of about 0.10 to about 0.35 grams per cubic centimeter. The absorbent core 44 may or may not be wrapped or encompassed by a suitable tissue wrap that maintains the integrity and/or shape of the absorbent assembly.

The outer cover 46 desirably includes a material that is substantially liquid impermeable, and can be elastic, stretchable or nonstretchable. The outer cover 46 can be a single layer of liquid impermeable material, but desirably includes a multi-layered laminate structure in which at least one of the layers is liquid impermeable. For instance, the outer cover 46 can include a liquid permeable outer layer and a liquid impermeable inner layer that are suitably joined together by a laminate adhesive (not shown). Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. The liquid permeable outer layer can be any suitable material and desirably one that provides a generally cloth-like texture. One example of such a material is a spunbond polypropylene nonwoven web having a basis weight of about 1 to about 100 gsm, suitably about 10 to about 30 gsm, more suitably about 20 gsm. The outer layer may also be made of those materials of which the first layer 20 is made. While it is not a necessity for the outer layer to be liquid permeable, it is desired that it provides a relatively cloth-like texture to the wearer.

The inner layer of the outer cover 46 can be both liquid and vapor impermeable, or can be liquid impermeable and vapor permeable. The inner layer is desirably manufactured from a thin plastic film, although other flexible liquid impermeable materials may also be used. The inner layer, or the liquid impermeable outer cover 46 when a single layer, prevents waste material from wetting articles, such as bed-sheets and clothing, as well as the wearer and caregiver. A suitable liquid impermeable film for use as a liquid impermeable inner layer, or a single layer liquid impermeable outer cover 46, is a polyethylene film having a thickness of about 0.2 to about 2.0 mil, suitably about 1.0 mil. If the outer cover 46 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 46. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn.

While the invention has been described in detail with respect to specific embodiments thereof, it will be appreciated to those skilled in the art, upon attaining an understanding of the foregoing may readily conceive of alterations to, variations of and equivalents to these embodiments. Accordingly, the scope of the present invention should be assessed as that of the appended claims and any equivalents thereto.

What is claimed is:

1. A composite material, comprising:
    a first layer forming a plurality of apertures; and
    a substructure bonded to the first layer at a plurality of bonding locations to form a plurality of compartments, the first layer apertures forming fluid communication between the first layer and the substructure and the compartments entrapping particles contained within a fluid which passes.

2. The composite material of claim 1, wherein the compartments have a triangular cross section.

3. The composite material of claim 1, wherein each compartment has a height of about 0.1 cm to about 2.0 cm.

4. The composite material of claim 1, wherein each compartment has a width of about 0.1 cm to about 2.0 cm.

5. The composite material of claim 1, wherein the first layer comprises a film.

6. The composite material of claim 1, wherein the first layer comprises a film and fiber combination.

7. The composite material of claim 1, wherein the first layer comprises a spunbond material.

8. The composite material of claim 1, wherein the first layer comprises a hydrophobic material.

9. The composite material of claim 1, wherein the first layer includes a plurality of apertures having a diameter of about 100 microns to about 10,000 microns.

10. The composite material of claim 1, wherein the first layer has a basis weight of about 0.3 osy to about 2.5 osy.

11. The composite material claim 1, wherein the first layer has a basis weight of about 0.44 osy to about 1.0 osy.

12. The composite material of claim 1, wherein the substructure comprises a three-dimensional nonwoven material.

13. The composite material of claim 1, wherein the substructure comprises a spunbond material.

14. The composite material of claim 1, wherein the substructure comprises a melt spun material.

15. The composite material of claim 1, wherein the substructure is pleated, corrugated, thermoformed or embossed.

16. The composite material of claim 1, wherein the substructure is bonded to the first layer by one of point bonding, adhesive bonding and spiral bonding.

17. A personal care absorbent product comprising the composite material of claim 1.

18. The composite material of claim 1, wherein the material is one of a spacer layer, a fastener, a filter medium, an air filter, a liquid filter, a facemask, and a wipe.

19. A combination comprising:
    a liquid permeable composite material of claim 1;
    an outer cover bonded to the liner; and
    an absorbent core positioned between the outer cover and the liner.

20. The composite material of claim 1, wherein the substructure is pleated.

21. A feminine hygiene product comprising the composite material of claim 1.

22. A wound care product comprising the composite material of claim 1.

23. A diaper comprising the composite material of claim 1.

24. Training pants comprising the composite material of claim 1.

25. Swim wear comprising the composite material of claim 1.

26. Absorbent underpants comprising the composite material of claim 1.

27. An adult incontinence article comprising the composite material of claim 1.

* * * * *

UNITED STATES PATENT AND TRADEMARK OFFICE
CERTIFICATE OF CORRECTION

PATENT NO. : 6,869,670 B2
DATED : March 22, 2005
INVENTOR(S) : Mary Lucille Delucia et al.

It is certified that error appears in the above-identified patent and that said Letters Patent is hereby corrected as shown below:

Title page,
Item [54], Title, change "COMPOSITES" to -- COMPOSITE --.

Signed and Sealed this

Nineteenth Day of July, 2005

JON W. DUDAS
*Director of the United States Patent and Trademark Office*